United States Patent
Cierullies

(10) Patent No.: US 9,678,008 B2
(45) Date of Patent: Jun. 13, 2017

(54) DEVICE FOR MEASURING SCATTERED LIGHT FROM A MEASUREMENT VOLUME WITH COMPENSATION FOR BACKGROUND SIGNALS

(71) Applicant: DURAG GmbH, Hamburg (DE)

(72) Inventor: Sven Cierullies, Hamburg (DE)

(73) Assignee: DURAG GMBH, Hamburg (DE)

( * ) Notice: Subject to any disclaimer, the term of this patent is extended or adjusted under 35 U.S.C. 154(b) by 0 days.

(21) Appl. No.: 14/893,858

(22) PCT Filed: May 30, 2014

(86) PCT No.: PCT/EP2014/061251
§ 371 (c)(1),
(2) Date: Nov. 24, 2015

(87) PCT Pub. No.: WO2014/191550
PCT Pub. Date: Dec. 4, 2014

(65) Prior Publication Data
US 2016/0123875 A1    May 5, 2016

(30) Foreign Application Priority Data
May 31, 2013 (EP) .................... 13002810

(51) Int. Cl.
*G01N 21/00* (2006.01)
*G01N 21/49* (2006.01)
(Continued)

(52) U.S. Cl.
CPC ......... *G01N 21/49* (2013.01); *G01N 15/0211* (2013.01); *G01N 21/53* (2013.01);
(Continued)

(58) Field of Classification Search
CPC ....... G01N 15/0211; G01N 2021/4709; G01N 2021/473; G01N 2021/536; G01N 21/49; G01N 21/53; G01N 2201/064
(Continued)

(56) References Cited

U.S. PATENT DOCUMENTS

| | | |
|---|---|---|
| 4,166,960 A | 9/1979 | Meili |
| 4,830,494 A | 5/1989 | Ishikawa et al. |
| 2011/0255087 A1 | 10/2011 | Alexander et al. |

FOREIGN PATENT DOCUMENTS

| | | |
|---|---|---|
| CH | 600 456 A5 | 12/1976 |
| EP | 0 360 126 A2 | 3/1990 |
| EP | 1 983 328 B1 | 10/2008 |

*Primary Examiner* — Tri T Ton
(74) *Attorney, Agent, or Firm* — Vidas, Arrett & Steinkraus, P.A.

(57) ABSTRACT

A device for measuring scattered light from a measurement volume with compensation for background signals, includes a light sensor having separately evaluable light-sensitive elements, a single imaging optical system, wherein the light-sensitive elements are arranged in the image plane and the measurement volume is arranged in the corresponding object plane of the optical system, a light transmitter with a collimated light beam, this light-sensitive element detects scattered light from the measurement volume and background light from the overlapping visual ranges behind the subject plane, and the other light-sensitive element detects no or significantly less scattered light from the measurement volume and background light from the overlapping visual areas behind the object plane, and a diaphragm that restricts the visual ranges of the light-sensitive elements behind the object plane.

14 Claims, 2 Drawing Sheets

(51) Int. Cl.
*G01N 21/53* (2006.01)
*G01N 15/02* (2006.01)
*G01N 21/47* (2006.01)

(52) U.S. Cl.
CPC ............... *G01N 2021/473* (2013.01); *G01N 2021/4709* (2013.01); *G01N 2021/536* (2013.01); *G01N 2201/064* (2013.01)

(58) Field of Classification Search
USPC .................................................. 356/335–343
See application file for complete search history.

DEVICE FOR MEASURING SCATTERED LIGHT FROM A MEASUREMENT VOLUME WITH COMPENSATION FOR BACKGROUND SIGNALS

CROSS-REFERENCE TO RELATED APPLICATIONS

This application is a national stage entry from PCT/EP2014/061251 filed on May 30, 2014 claiming priority of the European Patent Application No. 13 002 810.3 dated May 31, 2013.

BACKGROUND OF THE INVENTION

The present invention relates to a device for measuring scattered light from a measurement volume with compensation for background signals.

The measurement of scattered light is a well-known and trusted method for determining the concentration of dust or other particles in gaseous media. For instance, it is used in the measurement of the emissions of combustion plants. For that matter, a light beam coming from a sensor head is emitted into a measurement volume, which is scattered back by the particles. This scattered light is detected by the sensor head and is a measure for the particle concentration in the measurement volume.

In the measurement of scattered light, the measured power of the scattered light is very small in relation to the irradiated power. By multiple reflections and scattering, the light emitted by the sensor head generates background light in the surroundings of the measurement volume, which is also detected by the sensor head. For this reason, the sensor head provides a measurement signal resulting from the scattered light from the measurement volume, and a background signal resulting from background light. The strength of the background signal is in the order of magnitude of the measurement signal. In measurements within a chimney or another enclosed space, a strong background signal is caused by reflections and scattering on the wall opposite to the sensor head (called "background wall" in the following).

It is known to suppress the background light by a light trap, that is to say by a suitable device on the background wall opposite to the sensor head. It is furthermore known to measure the background light by a separate control receiver and to compensate it by calculation.

The documents DE 27 54 139 A1 and CH 600 456 describe a smoke detector, which uses both of these procedures. In one embodiment, two radiation receiving units are arranged behind on single lens. The fields of view of the two radiation receiving units have their focus at two neighbouring points, one of which is located within a radiation beam of a light transmitter. The two fields of view partly overlap each other on the opposing wall. The light transmitter is arranged vertically to the optical axis of the lens. Due to the only partial overlap of the fields of view, any complete compensation of the background radiation, which the light receiver directed to the measurement volume receives, is not possible.

The document EP 1 983 328 B1 describes a measurement device for determining a particle concentration within a measurement range, which works also with a measurement unit having a measurement receiver for the measurement signal and a control unit with a control receiver. When the device is being built in, the control receiver must be aligned such that it looks onto the same background as the measurement receiver. For the adjustment of the measurement device when it is being started or for maintenance works, a changing device is built in into the measurement unit and into the control unit, by which the measurement receiver and the control receiver can be changed by an adjustment light source, so that the effective cross section of the beam of the control light lobe and the measurement light lobe is visible for the human eye. The adjustment is sumptuous. In the adjustment, the beam cross sections are made coincident on a background wall of that room in which the measurement volume is situated. New adjustment is necessary in every new measurement situation. Moreover, the high space requirement of the optics is cumbersome when a measurement has to be performed across an opening in a wall. Finally, the adjustment light sources must be aligned exactly to the measurement receiver and the control receiver, which necessitates a high installation effort.

BRIEF SUMMARY OF THE INVENTION

Starting from this, the present invention is based on the goal to provide a measurement of scattered light with compensation for background signals, which needs only a small wall opening at measurements in an enclosed space, and wherein any adaptation to different distances to a background wall is not necessary or requires only a small expenditure.

The device for measuring scattered light from a measurement volume with compensation for background signals according to the present invention comprises

- at least one light sensor having at least two separately evaluable light-sensitive elements,
- a single imaging optical system, wherein the light-sensitive elements are arranged in the image plane and the measurement volume is arranged in the corresponding object plane of the optical system, the visual ranges of the light-sensitive elements are completely separate from each other in the object plane and overlap each other behind the object plane,
- a light transmitter with a collimated light beam, which only passes or at least primarily passes through the visual range of the one light-sensitive element within an area extending through the object plane and bordering the measured volume such that this light-sensitive element detects scattered light from the measurement volume and background light from the overlapping visual ranges behind the subject plane, and the other light-sensitive element detects no or significantly less scattered light from the measurement volume and background light from the overlapping visual areas behind the object plane, and
- a diaphragm that is arranged between the optical system and the light-sensitive elements and that restricts the visual ranges of the light-sensitive elements behind the object plane such that the areas of the two visual ranges which do not overlap each other are partially or completely hidden.

The device of the present invention uses at least one light sensor having two or more light-sensitive elements, such that the one light-sensitive element receives scattered light from the measurement volume and background light, whereas the other light-sensitive element receives no or significantly less scattered light and background light. For this purpose, an imaging optical system is used, such that the light-sensitive elements are placed into the image plane, whereas the measurement volume is located in the object plane that corresponds to the image plane. Whereas the two light-sensitive elements in the object plane have completely separated visual areas, the visual areas of the two light-sensitive elements overlap behind the object plane. The visual areas behind the object plane are disposed in a farther distance from the light-sensitive elements than the object plane. In particular, the visual areas of the light-sensitive elements overlap on a background wall. The two light-sensitive elements detect background light from the overlap area of the two visual areas to the same degree, i.e. from the area where the two visual areas overlap. In order to match the background signals provided by the two light-sensitive elements, a diaphragm is arranged between the optical system and the light-sensitive elements, which restricts the visual areas of the light-sensitive elements behind the object plane. The not overlapping areas of the two visual areas will be partly or completely hidden by the diaphragm, so that the two light-sensitive elements receive to a high degree or just only background light from the overlapping areas of the two visual areas. Through this, the background signals provided by the light-sensitive elements can be matched better or be made completely coincident. As a consequence, the device of the present invention provides additional reduction or suppression of the disturbance impact of background radiation. Because the device necessitates only one single imaging optical system for both measurement channels, it necessitates only a small wall opening and requires no adaptation to different distances of a background wall, depending on the required quality of the background correction.

The collimated light beam which generates the measurement signal by backward scattering, is emitted by a light transmitter such that it passes through the area overlooked by the one single light-sensitive element only or at least to a higher degree, particularly in the object plane, and passes through the visual area of the other light-sensitive element not at all or to a smaller degree. The area within which the light beam passes through the visual area of the one light-sensitive element limits the measurement volume.

According to one embodiment, an evaluation device is connected to the light sensor that detects the measurement signals supplied from the light-sensitive elements that originate of scattered light from the measured volume, wherein the evaluation device compensates the background signals originating from background light. The compensation of the background signals is preferably performed in that the signals of the other light-sensitive element are subtracted from the signals of the one light-sensitive element. The evaluation device is preferably an analogous evaluation electronics or an electronic data processing device (for instance a PC).

As an alternative, the signals of the light-sensitive elements are memorised and evaluated later. The device will be preferably provided with an evaluation device by the producing company. Alternatively, the producing company provides the device without evaluation device, and the user completes it by an evaluation device where necessary.

According to one embodiment, the diaphragm is arranged in the image plane of a background wall. By this arrangement, it is achieved that the visual areas of the two light-sensitive elements overlap each other exactly on the background wall.

According to another embodiment, the diaphragm is arranged in the image side focal point of the optical system. By this arrangement, it is achieved that the visual areas of the two light-sensitive elements overlap each other exactly in the infinity. This embodiment provides improved compensation of the background signals compared to a device without diaphragm. It may be used in particular for measurements with a far remote background wall or for measurements without adjustment of the optics.

From the well known lens equation for optical systems, at focal length f for an image distance B belonging to an object distance G results $$B = \frac{1}{\frac{1}{f} - \frac{1}{G}}$$

The corresponding image distances of the measurement volume $G_{MV}$ and of the background wall $G_{BH}$ result depending on the position of the measurement volume $B_{MV}$ and the background wall at $B_{HG}$.

Depending on the dimension of the light-sensitive elements, the maximum aperture of the diaphragm can be calculated from the condition that every spot on the light-sensitive element must have the same aperture angle with respect to the height of the imaging element A.

According to this calculation, in a further embodiment the diaphragm has an aperture which has maximally the value calculated by the following formula:

$$h_{Blende} = -h_{Det} + \frac{B_{MV} - B_{HG}}{B_{MV}}\left(\frac{A}{2} + h_{Det}\right)$$

wherein the following holds true:
 $h_{Blende}$=maximum height or half aperture of the diaphragm
 $h_{Det}$=height or half diameter of the detector
 $B_{MV}$=image distance of the measurement volume
 $B_{BW}$=image distance of the background wall
 A=diameter of the imaging system.

According to one embodiment, the device comprises a diaphragm with adjustable aperture and/or means for displacing the diaphragm toward the optical axis of the optical system. This permits adjustment by displacing and varying the diaphragm at different distances of the measurement device from a background wall. However, with suitable selection of focal length and diameter of the imaging optical element and with great distance of the background wall in relation to the object plane of the measurement area, such an adjustment is not necessary. Instead, a fixed adjustment of the diaphragm is suitable for a wide range of distances of the background wall from the optical system. This is due to the utilisation of one single optical system for both measurement channels, by which very flat angles of intersection result in the area of the object plane.

According to a further embodiment, the optical system comprises at least one lens or a concave mirror. Preferably, the optical system consists of at least one lens or a concave mirror.

According to a further embodiment, the light transmitter comprises a laser and/or a LED.

According to a further embodiment, the light-sensitive elements are constructionally formed in one single light sensor, for instance in a segmented photo diode. According to another embodiment, the light-sensitive elements are constructionally formed in different light sensors, e.g. in several photo diodes. Further, the present invention encompasses embodiments which comprise more than two light-sensitive elements, for instance in one segmented photo diode or in plural photo diodes or in a CMOS- or in a CCD-sensor. The light-sensitive elements have preferably flat light-sensitive surfaces.

According to one embodiment, the light transmitter is aligned at sharp angle relative to the optical axis of the imaging optical system. In this embodiment, the device can be directed to the measuring volume through one single wall opening. According to a further embodiment, the light beam or the light transmitter is arranged on the side next to the optical system, preferably in a short distance from the optical system. In a less preferred embodiment, imaging optical system and light transmitter are spatially separated from each other, for instance in that the light transmitter is directed vertically or in an obtuse angle relative to the optical axis of the imaging optical system.

BRIEF DESCRIPTION OF THE SEVERAL VIEWS OF THE DRAWINGS

The present invention will be explained in more detail in the following by way of the attached drawings. In the drawings show.

DETAILED DESCRIPTION OF THE INVENTION

Figure 1:
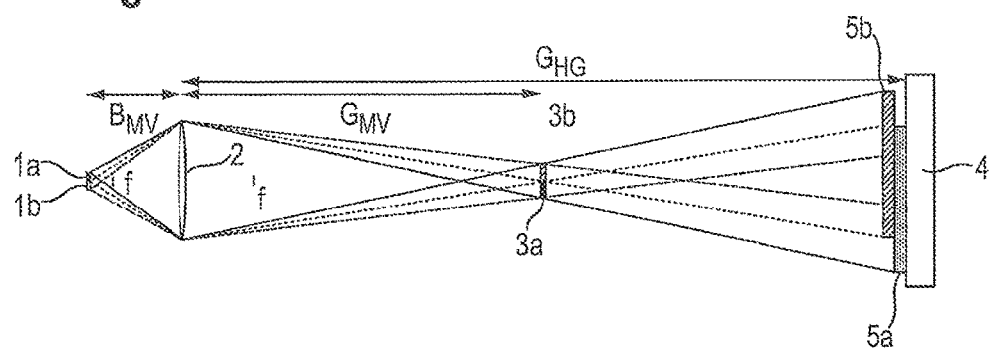
FIG. 1 a conventional device in a roughly schematic side view.

In the following explanation of different realisation examples, coincident or essentially coincident components and details of the light path are provided with coincident reference numerals.

While this invention may be embodied in many different forms, there are described in detail herein a specific preferred embodiment of the invention. This description is an exemplification of the principles of the invention and is not intended to limit the invention to the particular embodiment illustrated.

According to FIG. 1, a light sensor 1 has two or more separately evaluable light-sensitive elements 1a, 1b. The segmented light sensor 1 is situated in the image plane of an imaging system 2 in the form of a biconvex lens. The measurement volume is in the corresponding object plane.

Whereas the visual ranges 3a, 3b of the light-sensitive elements 1a, 1b are completely separate from each other in the object plane, the visual ranges overlap each other outside of object plane. The visual ranges 5a, 5b overlap each other on a background wall 4. As a result, the light-sensitive elements 1a, 1b measure a similar, but not the same background radiation.

Figure 2:
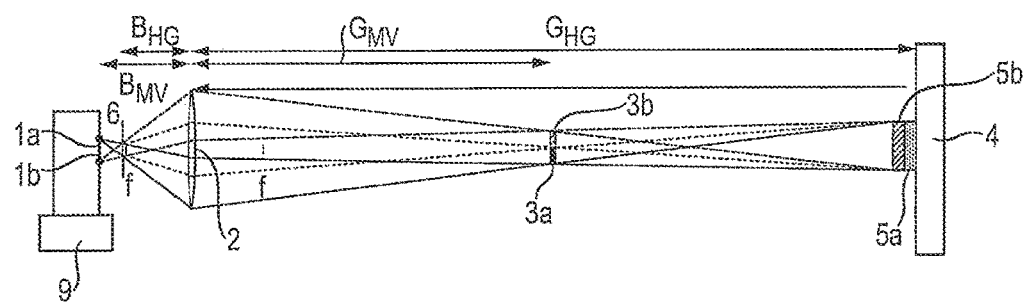
FIG. 2 a device according to the present invention with diaphragm in the image plane of a background wall, in a roughly schematic side view.

According to FIG. 2, a harmonisation of the visual ranges 5a, 5b on the background wall 4 is achieved by a diaphragm 6, which is arranged in the image plane of the background wall. Through this arrangement of the diaphragm 6, the ranges 5a, 5b imaged in the background overlap exactly.

Figure 3:
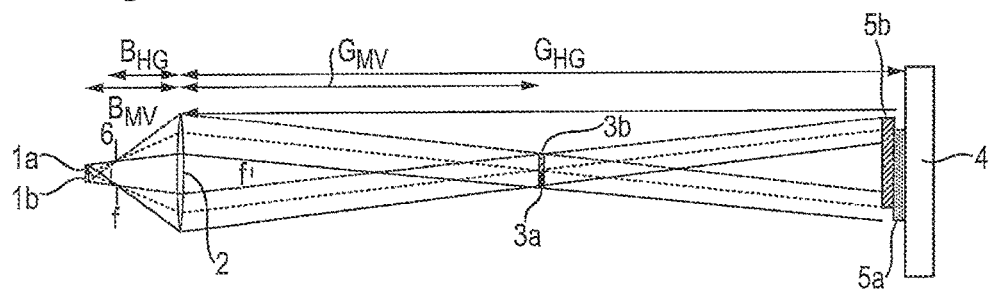
FIG. 3 a device according to the present invention with diaphragm in the image side focal point of the imaging optical system in a roughly schematic side view.

FIG. 3 shows a special case, where the background wall 4 is assumed in the optically seen infinite. In this case, the diaphragm 6 is placed in the image side focal point of the lens 2, and the beams, which define the image on the wall, run in parallel.

In the realisations of FIGS. 2 and 3, the imaging optical system may consist of one lens 2 as well as of plural lenses.

Figure 4:
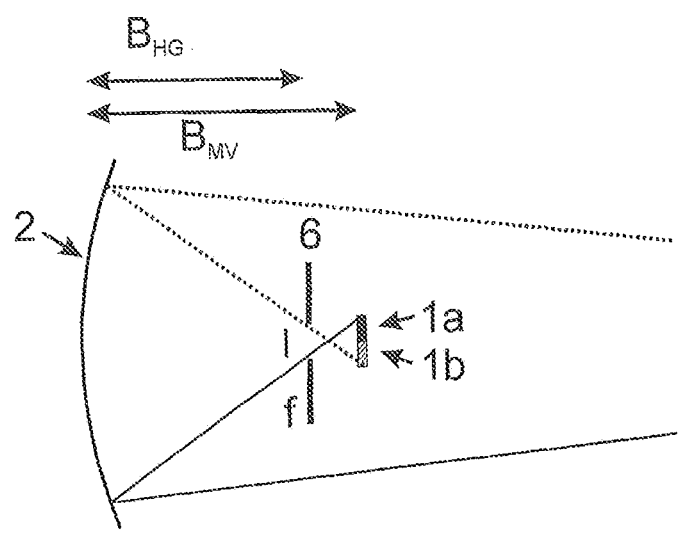
FIG. 4 a device according to the present invention with a concave mirror as imaging optical system in a roughly schematic partial side view.

In the realisation of FIG. 4, the imaging optical system is realised as a concave mirror 2. In this realisation, the light sensor 1 with the light-sensitive elements 1a, 1b is situated between the concave mirror 2 and the measurement volume, and the diaphragm 6 is situated between the light sensor 1 and the concave mirror 2. In this example, the diaphragm 6 is placed in the image plane of the background wall. For the rest, the light path is according to FIG. 2 in this realisation. The symmetry axis of the concave mirror is advantageously in a small angle to the optical axis of the system, so that the diaphragm 6 and the elements 1a, 1b do not shadow the incident light with respect to the concave mirror 2. Thus, the elements 1a, 1b are arranged before or respectively behind the plane of projection of FIG. 4.

Figure 5:
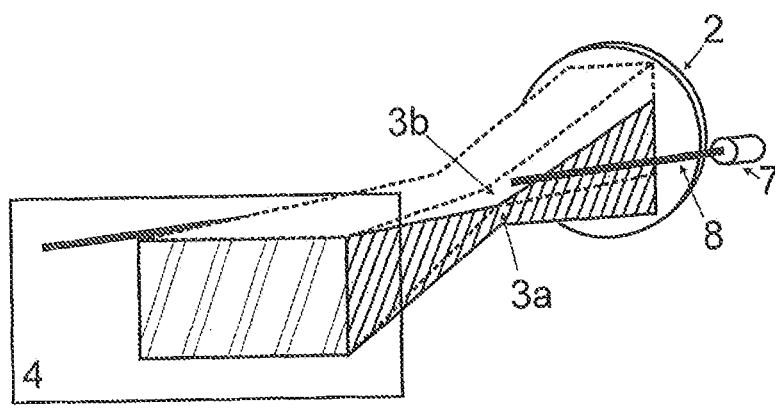
FIG. 5 the arrangement of the light transmitter and the path of the light beam in the measurement device in a roughly schematic perspective view.

According to FIG. 5, a collimated light transmitter 7 emits a light beam 8 from a position laterally next to the imaging optical system 2 in a sharp angle to the optical axis of the imaging optical system 2 such that the same passes in the image plane only through the range 3b which the one light-sensitive element 1b looks up. On the contrary, the light beam 8 does not pass through the range 3a, which is looked up by the other light-sensitive element 1a. Before and behind the object plane, the light beam passes only through the visual range of the one light-sensitive element 1b. The complete range in which the light beam 8 passes through the visual range of the one light-sensitive element 1b limits the measurement volume.

According to FIG. 2, an evaluation device 9 is connected to the light sensor 1, which determines the measurement signal originating of scattered light from the signals provided by the light-sensitive elements 1a, 1b by compensating the background signal.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A device for measuring scattered light from a measurement volume with compensation for background signals, comprising at least one light sensor having at least two separately evaluable light-sensitive elements, a single imaging optical system, wherein the light-sensitive elements are arranged in the image plane and the measurement volume is arranged in the corresponding object plane of the optical system, the visual ranges of the light-sensitive elements are completely separate from each other in the object plane and overlap each other behind the object plane, a light transmitter with a collimated light beam, which only passes through, or at least primarily passes through, the visual range of the one light-sensitive element within an area extending through the object plane and bordering the measured volume such that this light-sensitive element detects scattered light from the measurement volume and background light from the overlapping visual ranges behind the subject plane, and the other light-sensitive element detects no or significantly less scattered light from the measurement volume and background light from the overlapping visual areas behind the object plane, and a diaphragm that is arranged between the optical system and the light-sensitive elements that restricts the visual ranges of the light-sensitive elements behind the object plane such that the areas of the two visual ranges which do not overlap each other are partially or completely hidden.

2. The device according to claim 1, wherein the light transmitter is aligned such that the light beam only passes through the visual range of the one light-sensitive element.

3. The device according to claim 1, wherein the diaphragm restricts the visual range of the light-sensitive elements to the overlapping area of the two visual ranges such that the two light-sensitive elements detect background light to the same degree.

4. The device according to claim 1, further including an evaluation device that is connected to the at least one light sensor and that detects the amount of the measurement signals supplied from the light-sensitive elements that originates from the measured volume, wherein the evaluation device compensates for the amount originating from the background light.

5. The device according to claim 1, wherein the diaphragm is arranged in the image plane of a background wall.

6. The device according to claim 1, wherein the diaphragm is arranged in the image side focal point of the optical system.

7. The device according to claim 1, wherein the diaphragm has an aperture that has at most the value calculated according to the following formula:

$$h_{Blende} = -h_{Det} + \frac{B_{MV} - B_{HG}}{B_{MV}}\left(\frac{A}{2} + h_{Det}\right)$$

wherein the following holds true:

$h_{Blende/Diaphragm}$=maximum height or half aperture of the diaphragm
$h_{Det}$=height or half diameter of the detector
$B_{MV}$=image distance of the measurement volume
$B_{BW}$=image distance of the background wall
A=Diameter of the imaging system.

8. The device according to claim 1, further including a diaphragm with an adjustable aperture or means for displacing the diaphragm toward the optical axis of the optical system.

9. The device according to claim 1, wherein the optical system comprises a lens or concave mirror.

10. The device according to claim 1, wherein the light transmitter comprises a laser or LED.

11. The device according to claim 1, wherein the light-sensitive elements are formed in a single light sensor.

12. The device according to claim 1, wherein the light-sensitive elements are formed in different light sensors.

13. The device according to claim 1, wherein the light transmitter is aligned at a sharp angle relative to the optical axis of the imaging optical system.

14. The device according to claim 13, wherein the light transmitter or the light beam is arranged on the side next to the optical system.

* * * * *